(12) United States Patent
Dear et al.

(10) Patent No.: US 9,539,623 B2
(45) Date of Patent: Jan. 10, 2017

(54) CONTAINER TREATMENT

(76) Inventors: Lance Allen Dear, Hastings (NZ);
Richard John Newson, Hastings (NZ)

(*) Notice: Subject to any disclaimer, the term of this patent is extended or adjusted under 35 U.S.C. 154(b) by 413 days.

(21) Appl. No.: 13/504,515

(22) PCT Filed: Nov. 2, 2010

(86) PCT No.: PCT/NZ2010/000220
§ 371 (c)(1),
(2), (4) Date: Apr. 27, 2012

(87) PCT Pub. No.: WO2011/053171
PCT Pub. Date: May 5, 2011

(65) Prior Publication Data
US 2012/0230866 A1    Sep. 13, 2012

(30) Foreign Application Priority Data
Nov. 2, 2009  (NZ) ........................................ 580870

(51) Int. Cl.
| | |
|---|---|
| *A61L 2/04* | (2006.01) |
| *B08B 7/00* | (2006.01) |
| *A61L 2/06* | (2006.01) |
| *B08B 5/00* | (2006.01) |
| *B08B 9/08* | (2006.01) |
| *A61L 2/07* | (2006.01) |
| *A61L 2/20* | (2006.01) |

(52) U.S. Cl.
CPC ............... *B08B 7/0071* (2013.01); *A61L 2/06* (2013.01); *B08B 5/00* (2013.01); *B08B 9/08* (2013.01); *A61L 2/07* (2013.01); *A61L 2/20* (2013.01); *A61L 2202/23* (2013.01)

(58) Field of Classification Search
CPC ................. A61L 2/04; A61L 2/07; A61L 2/20
USPC ...................................... 422/22, 307; 43/124
See application file for complete search history.

(56) References Cited

U.S. PATENT DOCUMENTS

| | | | |
|---|---|---|---|
| 4,911,317 A * | 3/1990 | Schloesser ........... | B65D 90/046 220/1.5 |
| 5,641,463 A * | 6/1997 | Langhart ....................... | 422/294 |
| 6,612,067 B2 * | 9/2003 | Topp ............................... | 43/124 |
| 6,984,359 B2 * | 1/2006 | Florkey et al. ................... | 422/3 |
| 7,908,791 B1 * | 3/2011 | Brash .............................. | 43/125 |
| 8,486,345 B1 * | 7/2013 | Westrum et al. ............. | 422/307 |
| 2003/0026727 A1 * | 2/2003 | Topp ............................... | 422/1 |
| 2004/0035044 A1 * | 2/2004 | Topp ............................... | 43/124 |

* cited by examiner

*Primary Examiner* — Sean E Conley
(74) *Attorney, Agent, or Firm* — Bio Intellectual Property Services LLC (BIO IPS); O. (Sam) Zaghmout

(57) ABSTRACT

A method of decontaminating a freight container comprising the steps of: a) placing a freight container on a support; b) using an enclosure to substantially enclose the container on the support; and c) applying heat so that hot air moves within the enclosure around at least upright ends, sides and a roof of the container to kill or substantially weaken undesired life forms on or immediately adjacent to the exterior of the container.

31 Claims, 5 Drawing Sheets

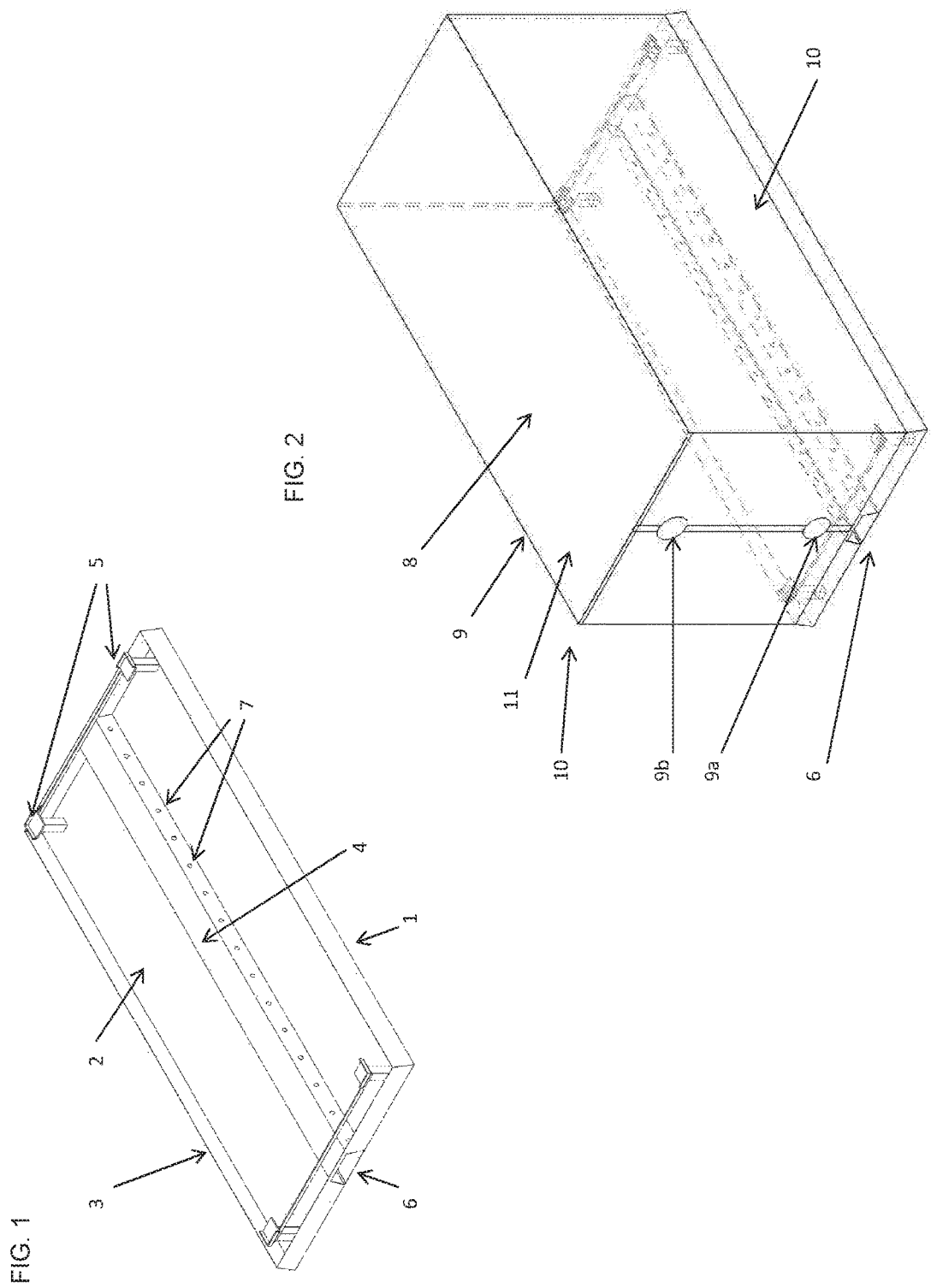

CONTAINER TREATMENT

FIELD OF INVENTION

This invention relates to the treatment of freight containers. A preferred form of the invention relates to the treatment of ISO freight containers of the type used for international shipping.

BACKGROUND

It is known to use large freight containers to hold goods and to ship these from one country to another. On arrival at the port of destination it is desirable to decontaminate the containers in case undesirable life forms, for example microbes, insects or other pests, have ridden the container from one country to another. It is an object of a preferred form of the invention to go at some way towards providing an useful alternative to known forms of container decontamination.

SUMMARY OF THE INVENTION

According to one aspect of the invention there is provided a method of decontaminating a freight container comprising the steps of:
a) placing a freight container on a support;
b) using an enclosure to substantially enclose the container on the support; and
c) applying heat so that hot air moves within the enclosure around at least upright ends, sides and a roof of the container, and underneath the container, to kill or substantially weaken undesired life forms on or immediately adjacent to the exterior of the container.

Optionally the support is heated prior to step a).

Optionally the support provides for an air gam beneath the container so that hot air flows underneath the container to kill or substantially weaken undesired life forms if on or immediately adjacent to the bottom of the container.

Optionally the exterior of the container is exposed to the heat for sufficient time to allow the heat to conduct into the interior of the container to kill or substantially weaken undesired life forms if within the container.

Optionally hot air is applied to the interior of the container to kill or substantially weaken undesired life forms if within the container.

Optionally the heat is sufficient to kill the undesired life forms and no chemicals are applied to the container.

Optionally decontamination chemicals are applied to only the exterior of the container, to the interior only, or to the exterior and interior of the container, so that the combination of heat and chemicals is sufficient to kill undesired life forms.

Optionally water vapour is applied to the container so that the combination of heat and water vapour is sufficient to kill the undesired life forms.

Optionally the enclosure comprises a flexible canopy.

Optionally the flexible canopy comprises one or more flexible sheets.

Optionally the enclosure comprises rigid walls in combination with one or more flexible sheets.

Optionally the container is an ISO container.

Optionally the container is a 40 foot long ISO container.

Optionally the container is a 20 foot long ISO container.

Optionally the container is subjected to the heat for approximately 30 minutes.

According to a further aspect of the invention there is provided a decontamination chamber suitable for use in the method set out above, the chamber having:
a) a supportive base;
b) an enclosure;
c) means for producing a flow of hot air; and
d) means for channelling air;
the chamber formed such that when it is in use it is able to receive a 20 or 40 foot long ISO certified freight container on the base, the enclosure can cause the container to be enveloped, the means for producing hot air can cause a flow of air so that the container is heated to more than 50° C., and the means for channelling air can cause the air to move across the underside, the end and side walls and the roof of the container to kill undesirable life forms associated with the container.

Optionally the means for channelling air comprises a space within the base and there are vents open to the upper surface of the base.

Optionally the chamber comprises an arrangement of vents adapted for providing a curtain of hot air around peripheral parts of the base.

Optionally the base comprises a tray.

Optionally the enclosure comprises a flexible air impermeable curtain.

Optionally the enclosure comprises a support frame which can swing to provide a support structure for the roof and front side of the enclosure.

Optionally the enclosure comprises rigid end walls and a rigid rear side wall.

Optionally the means for producing a flow of hot air causes the container to be heated to more than:
55° C.;
60° C.;
65° C.;
70° C.;
75° C.;
80° C.; or
85° C.

Optionally the decontamination chamber is portable and/or mobile.

BRIEF DESCRIPTION OF THE DRAWINGS

Some preferred forms of the invention with now be described by way of example and with reference to the accompanying images, of which:

FIG. 1 is an isometric view of a support tray for receiving a container;

FIG. 2 is an isometric view showing a freight container when situated on the tray;

DETAILED DESCRIPTION

Figure 3:
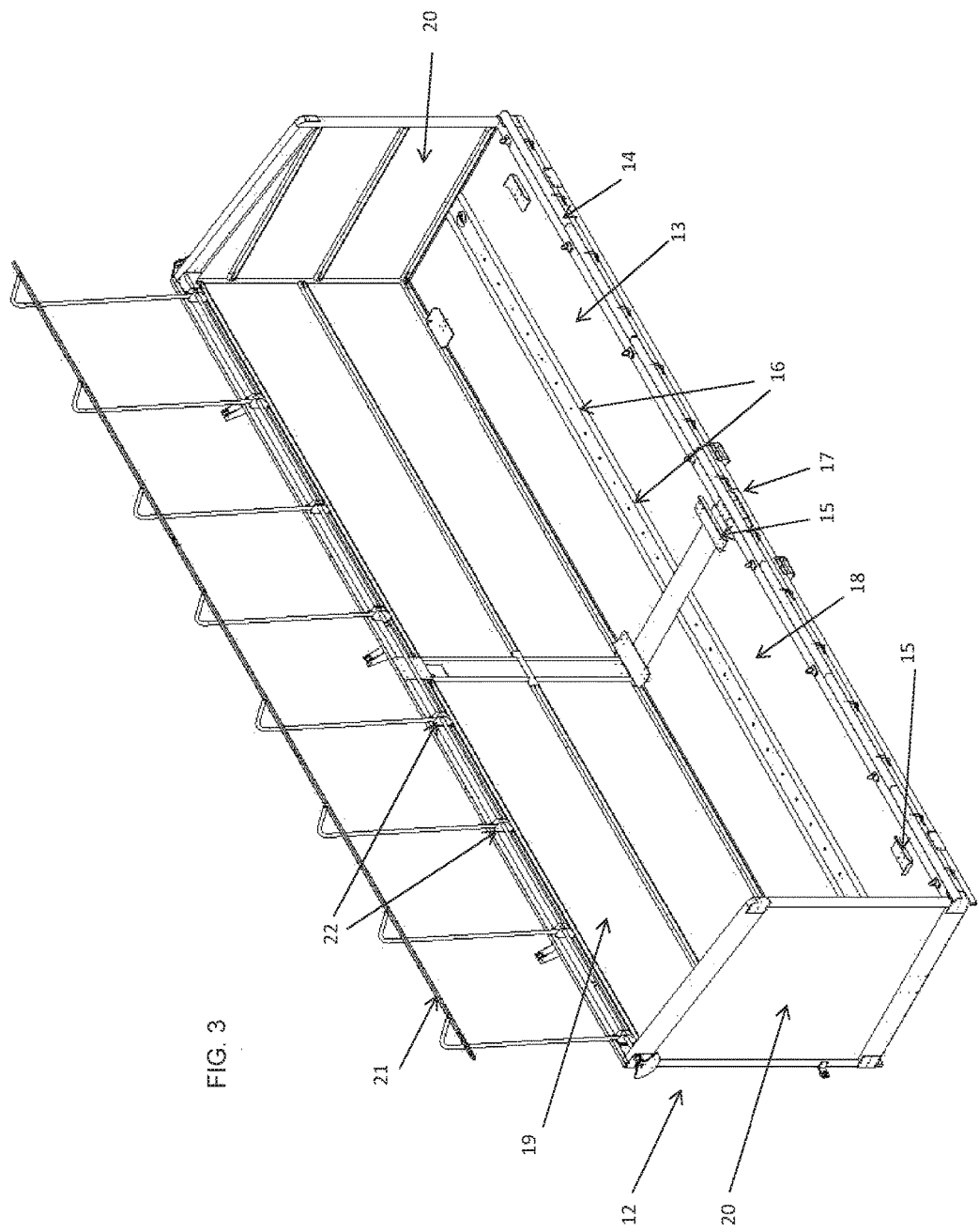
FIG. 3 is an isometric side view of a mobile decontamination chamber when open.

Referring to FIG. 1, one embodiment of the invention comprises a portable support tray 1 for receiving a freight container. The tray has a floor 2, inwardly inclined sides 3, a central conduit 4 and four upwardly extending legs 5. The conduit 4 is open at one end 6 so that it is able to receive a flow of air and also has a series of vents 7 along its length to enable the flow to be distributed across the floor 2.

Referring to FIG. 2, when the tray is in use an ISO grade freight container 8 may be placed on the legs 5 so that there is a space between the underside of the container and the floor 2 of the tray. The container 8 is covered by an air impermeable flexible enclosure 9 and this may be sealed to the tray. A flow of hot air is applied to the opening 6 of the conduit so that the air is driven along the conduit and distributed over the floor 2 of the tray via the vents 7. As the vents are relatively small the conduit 4 serves as a pressure accumulator for the hot air. The air moves to the edges of the tray 3 and then upwards around the ends, the sides 10 and roof 11 of the container. The inward incline of the sides 3 of the tray helps direct the flow of air upwards to substantially prevent it from escaping from the confines of the enclosure 9. Preferably the arrangement is such that when the air is flowing there is a space of approximately 100 mm between the ends, sides and roof of the container and the enclosure 9. In some embodiments a supplementary flow of hot air may be circulated into and out of the enclosure via openings 9a and 9b.

The hot air causes the external faces of the container to heat up and this kills at least most undesirable life forms at or adjacent to those faces. In preferred forms of the invention the air flow is set so that the container is heated to 56t to 60t and is maintained at that temperature for 30 minutes. The temperature chosen in any one situation may vary depending on the sensitivity of the contents of the container, if any. Higher temperatures may be applied to empty containers and in such cases the treatment time may be reduced. For example in cases where an empty container is heated to 85° C. the treatment time may be reduced to approximately 5 minutes.

In preferred embodiments of the invention the tray 1 is heated, to approximately 56° C. to 60° C. prior to placing the container on the tray. This assists to prevent at least some insects or other pests from escaping the decontaminating heat as they may otherwise detect a slowly increasing temperature and try leave the vicinity of the container before temperatures rise to a level sufficient to kill them.

Heat applied to the exterior surfaces of the container conducts through to the interior of the container. In some embodiments of the invention the amount of heat conducted is sufficient to decontaminate the inside of the container.

Figure 4:
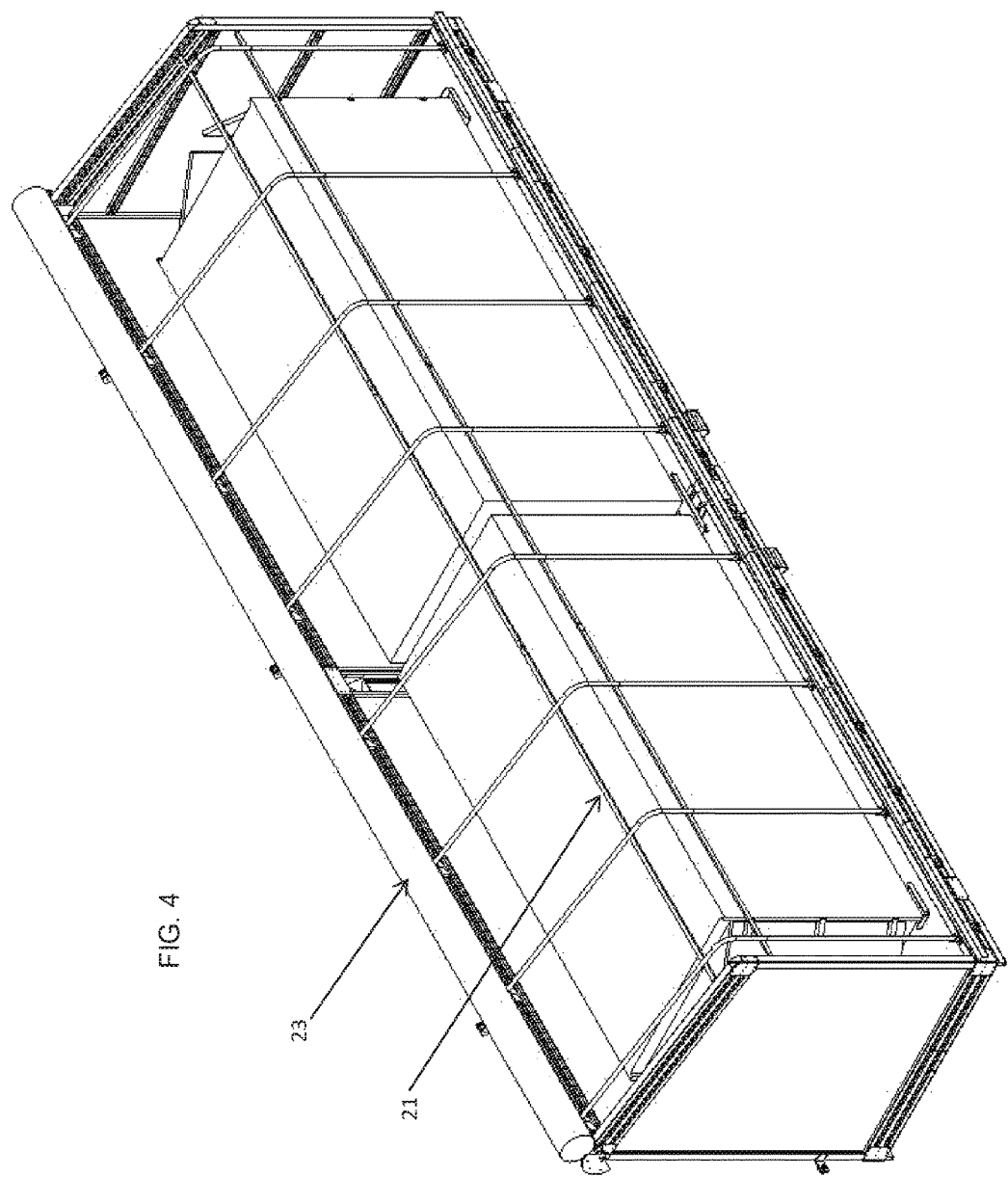
FIG. 4 is an isometric view of the chamber when loaded with a freight container.
Figure 5:
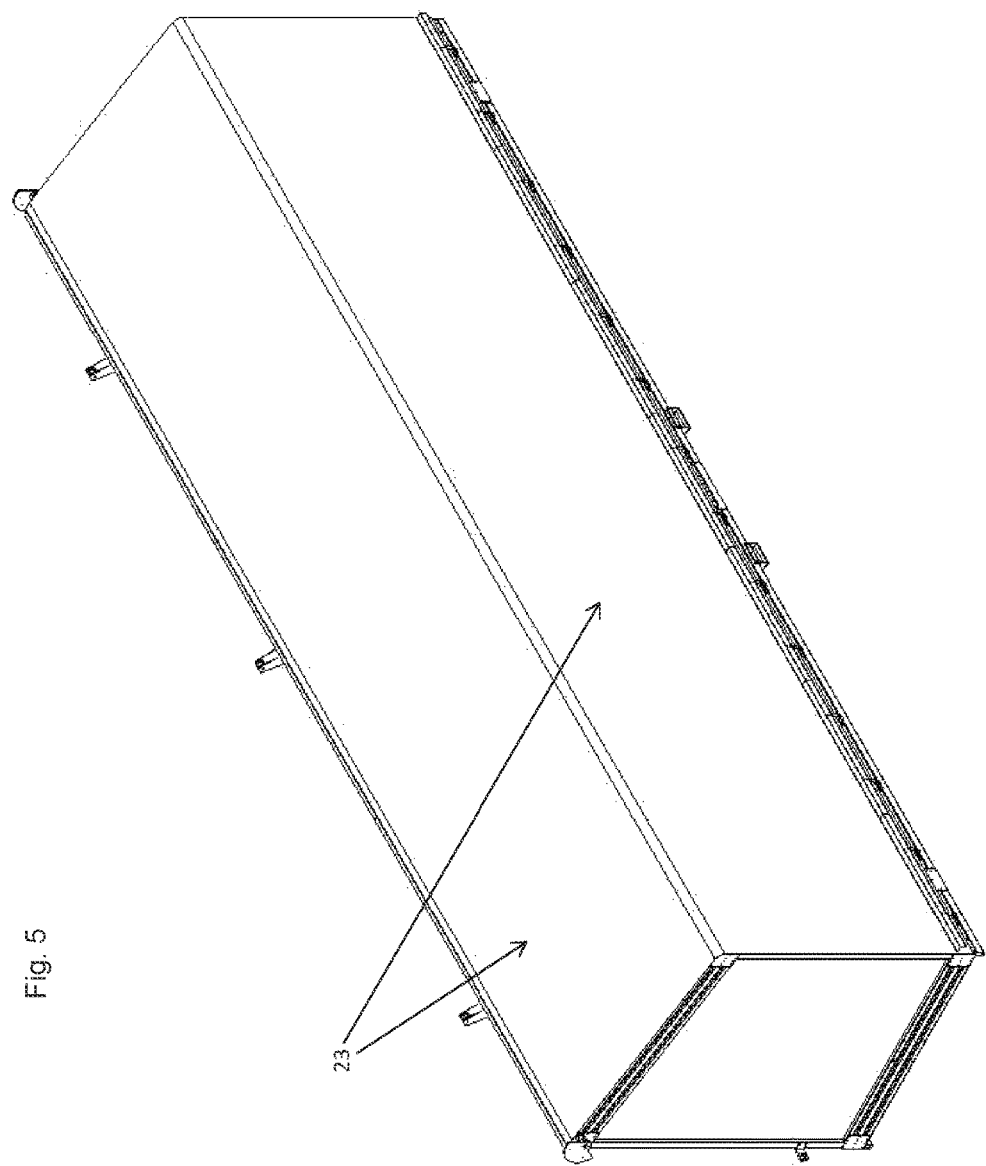
FIG. 5 is an isometric view of the chamber when loaded with the container and closed.

FIGS. 3, 4 and 5 show a portable decontamination chamber 12 according to an alternative embodiment of the invention. Referring to FIG. 3, the chamber has a support tray 13 comprising upper and lower rigid floor sheets arranged so that there is a space between them. The chamber also has an inwardly inclined forward side 14 and a series of legs 15. The space between the floor sheets provides a pressure accumulating conduit and there is a series of vents 16 spaced along the upper floor sheet to distribute a hot air flow across the upper surface 18 of the tray. The conduit has an opening 17 situated mid-way along the tray adjacent to its forward side 14 for receiving the air flow. Vent holes (not shown) are also situated at the edges of the tray 13, both at the upper surface of the tray and at the vertical sides of the tray, to allow the air flow to proceed therefrom and create a hot air curtain at the edges of the tray. The hot air curtain makes it difficult for certain life forms to escape the confines of the chamber. The chamber also has an enclosure comprising a rigid rear side wall 19, rigid end walls 20 and a frame 21. The frame 21 is arranged to pivot about hinges 22 so that it can provide a roof and front side structure.

FIG. 4 shows the chamber when a 40 foot ISO grade freight container has been placed on the feet of the tray. The frame 21 has been swung down by way of the hinges and is ready to support an air impermeable flexible curtain 23 which is illustrated in a rolled-up or stowed disposition.

Referring to FIG. 5, when the chamber is ready for use the curtain 23 is rolled down over the frame so that the container is completely enclosed. With the container in this situation hot air is pumped into the conduit space within the tray and from there the air moves around the floor, sides and roof of the container to kill undesired life forms, for example microbes, insects or rodents on or immediately adjacent to the exterior of the container. In some embodiments heat from the air also conducts through the walls of the container to decontaminate its interior. The temperature, the treatment time and the spacing between the container and the chamber may be the same as described for FIGS. 1 and 2.

Preferably the tray of the FIGS. 3, 4 and 5 embodiment is heated prior to locating the container within the chamber for the same reason described previously.

Figure 6:
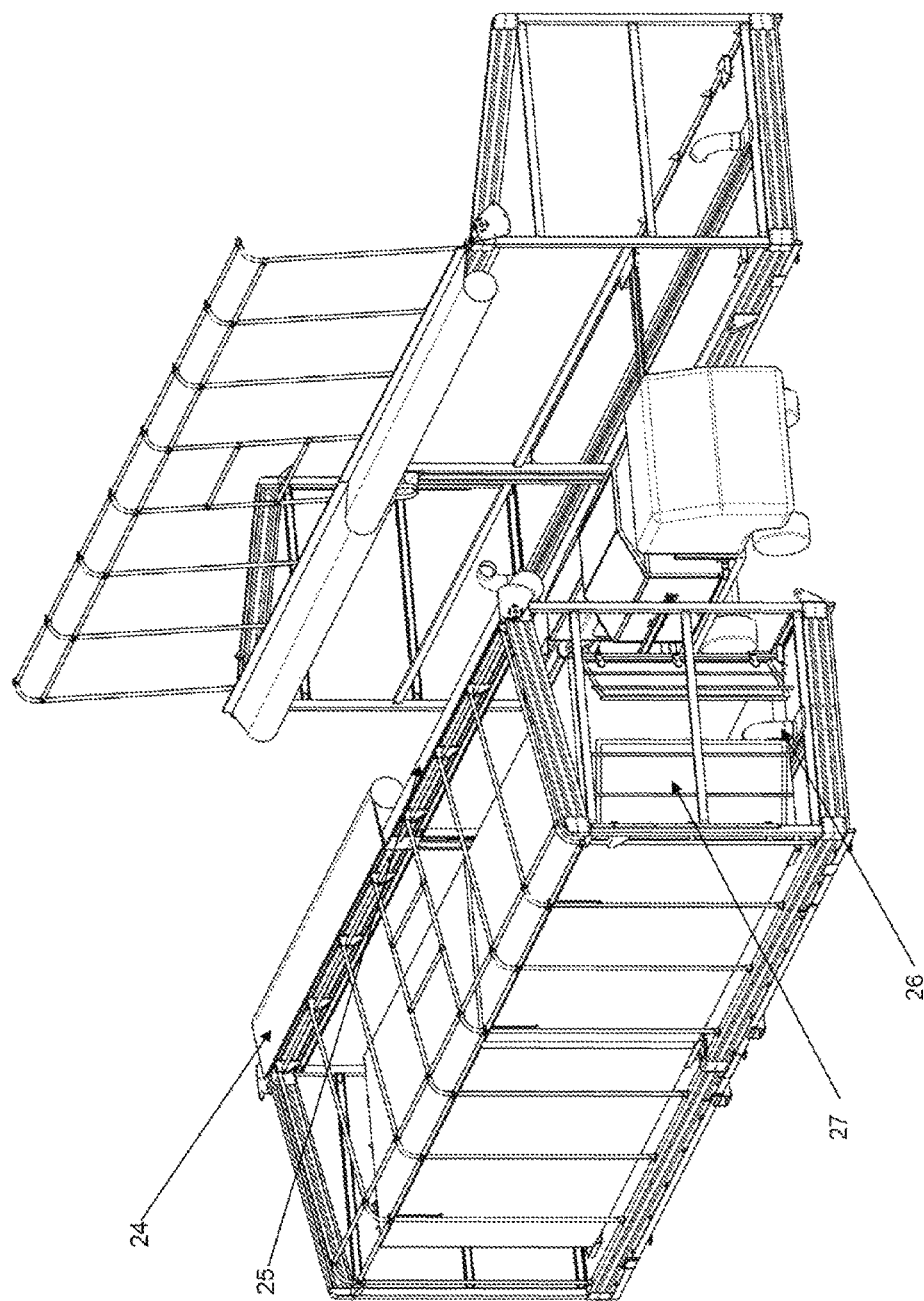
FIG. 6 is an isometric view of an alternative mobile decontamination chamber.

FIG. 6 illustrates two portable decontamination chambers similar to that described for FIGS. 3, 4 and 5, except that the flexible curtain in each case comprises two rolls 24, 25 rather than one. In this embodiment an air supply pipe 26 is arranged to direct a flow of hot air from the conduit into open doors 27 of the container to heat and thus decontaminate the inside of the container.

Preferably the tray for the FIG. 6 embodiment is heated prior to locating the container within the chamber for the same reason described previously.

In some embodiments of the invention a supplementary flow of hot air may be applied to the chambers of FIGS. 3 to 6 through a side wall of the enclosure.

In further embodiments of the invention the flow of hot air carries decontamination chemicals such as pesticides and/or water vapour. In such cases these may combine with the heat in the air to kill undesired life forms.

In some embodiments of the invention the inside of the container may be heated by way of heat (eg hot air) applied to exterior surfaces of the container, and the space within the container is subjected to a chemical fumigant arranged such that raising temperature within the container increases the efficiency of the fumigant. In this embodiment hot air is circulated around the outside of the container (ie without fumigant) and the fumigant is only applied within the container.

In preferred forms of the invention the hot is allowed to vent from the enclosure/chamber to be replaced by new hot air, rather than recirculating used air. This can facilitate control of humidity within the enclosure/chamber.

To achieve container temperatures sufficient for decontamination the hot air applied to the container may be at up to 200° C., but preferably from 75° C. to 175° C., and most preferably from 80° C. to 150° C. The air may be driven at up to 1,000 m$^3$/min, preferably between 200 m$^3$/min and 750 m$^3$/min, and most preferably between 250 m$^3$/min and 500 m$^3$/min. Preferably humidity within the enclosure/chamber is at 5% to 50%.

As will be appreciated, the portable nature of the tray and chambers described above means that they can be readily moved from one location to another, for example from one port or wharf to another. In some embodiments the tray or chambers may be mobile, for example they may have set of wheels and a motor to power these.

While some embodiments of the invention have been described by way of example it should be appreciated that modifications and improvements can occur without departing from the scope of the following claims.

The invention claimed is:

1. A method of decontaminating a freight container comprising the steps of:
   a) placing a freight container on a support base wherein the support base provides a pressure accumulating conduit, the pressure accumulating conduit including a series of vents and an opening, the support base also provides for an air gap beneath the container;
   b) using an enclosure to substantially enclose the container on the support; wherein the enclosure comprises a flexible roof and at least one flexible side and
   c) applying heat to an opening in the pressure accumulating conduit so that hot air moves through the pressure accumulating conduit and through the vents to distribute the air across the support base to the edges of the support base and upwards around the sides and a roof of the container, to kill or substantially weaken undesired life forms on or immediately adjacent to the exterior of the container.

2. A method according to claim 1, wherein the support is heated prior to step a).

3. A method according to claim 1, wherein the exterior of the container is exposed to the heat for sufficient time to allow the heat to conduct into the interior of the container to kill or substantially weaken undesired life forms if within the container.

4. A method according to claim 1, wherein decontamination chemicals are applied to the exterior of the container only, to the interior of the container only, or to the exterior and interior of the container, so that the combination of heat and chemicals is sufficient to kill undesired life forms.

5. A method according to claim 1, wherein water vapour is applied to the container so that the combination of heat and water vapour is sufficient to kill the undesired life forms.

6. A method according to claim 1, wherein the enclosure is an air impermeable flexible enclosure.

7. A method according to claim 1, wherein the container is an ISO container.

8. A method according to claim 1, wherein the container is a 40 foot long ISO container.

9. A method according to claim 1, wherein the container is a 20 foot long ISO container.

10. A method according to claim 1, wherein the container is subjected to the heat of approximately 30 minutes.

11. A method according to claim 1 further comprising the step of circulating a supplementary flow of hot air through openings in the enclosure.

12. A method according to claim 1 further comprising the step of providing an air supply pipe arranged to direct a flow of hot air into open doors of the container and providing hot air to the air supply pipe from the pressure accumulating conduit so as to decontaminate the inside of the chamber.

13. A method according to claim 1 further comprising the step of applying hot air at up to 200° C.

14. A method according to claim 13 further comprising the step of applying hot air between 75° C. and 175° C.

15. A method according to claim 13 further comprising the step of applying hot air between 80° C. and 150° C.

16. A method according to claim 1 further comprising the step of driving the hot air at up to 1000 m³/min.

17. A method according to claim 16 further comprising the step of driving the hot air at between 200 m³/min and 750 m³/min.

18. A method according to claim 16 further comprising the step of driving the hot air at between 250 m³/min and 500 m³/min.

19. A decontamination chamber suitable for use in the method of claim 1, the chamber having:
   a) a supportive base including a pressure accumulating conduit, the pressure accumulating conduit including a series of vents and open at one end to be able to receive hot air from a source of hot air through the open end;
   b) an enclosure comprising a flexible roof and at least one flexible side; and
   c) a hot air producing apparatus;
the chamber formed such that when it is in use it is able to receive a 20 or 40 foot long ISO certified freight container on the base, the enclosure can cause the container to be enveloped, the means for producing hot air can cause a flow of hot air to the pressure accumulating conduit so that the container is heated to more than 50° C., and the at least one pressure accumulating conduit for channelling air can cause the air to move across the underside, the end and side walls and the roof of the container to kill undesirable life forms associated with the container.

20. A decontamination chamber according to claim 19, wherein the chamber comprises an arrangement of vents adapted to provide a curtain of hot air around peripheral parts of the base.

21. A decontamination chamber according to claim 19, wherein the base comprises a tray.

22. A decontamination chamber according to claim 19, where the enclosure comprises a flexible air impermeable curtain.

23. A decontamination chamber according to claim 19, wherein the enclosure comprises a support frame which can swing upwards to provide a support structure for the roof and front side of the enclosure.

24. A decontamination chamber according to claim 19, wherein the enclosure comprises rigid walls and a rigid rear side wall.

25. A decontamination chamber according to claim 19, wherein the hot air producing apparatus causes the container to be heated to more than:
   55° C.;
   60° C.;
   65° C.;
   70° C.;
   75° C.;
   80° C.; or
   85° C.

26. A decontamination chamber according to claim 19, which is portable and/or mobile.

27. A decontamination chamber according to claim 21 wherein the tray comprises a floor, inwardly inclined sides, the pressure accumulating conduit and four upwardly extending legs.

28. A decontamination chamber according to claim 27 where the inwardly inclined sides of the tray direct air flow upwards.

29. A decontamination chamber according to claim 19 wherein the enclosure includes openings to allow a supplementary flow of hot air through the openings.

30. A decontamination chamber according to claim 19 further including an air supply pipe arranged to direct a flow of hot air from the conduit into open doors of the container to heat and thus decontaminate the inside of the container.

31. A method of decontaminating a freight container comprising the steps of:
   a) heating a support base;

b) placing a freight container on a support base wherein the support base provides a pressure accumulating conduit, the pressure accumulating conduit including a series of vents, the support base also provides for an air gap beneath the container;
c) using an enclosure to substantially enclose the container on the support base; wherein the enclosure comprises a flexible roof and at least one flexible side; and
d) applying heat at a temperature between 80° C. and 150° C. and a rate of between 250 m$^3$/min and 500 m$^3$/min to an opening in the pressure accumulating conduit so that hot air moves through the pressure accumulating conduit and through the vents to distribute the air across the support base to the edges of the support base and upwards around the sides and a roof of the container, to kill or substantially weaken undesired life forms on or immediately adjacent to the exterior of the container;
e) applying heat to openings in the enclosure to circulate a supplementary flow of hot air through the enclosure; and
f) providing an air supply pipe arranged to direct a flow of hot air into open doors of the container and providing hot air to the air supply pipe from the pressure accumulating conduit so as to decontaminate the inside of the chamber.

* * * * *